US007835529B2

(12) United States Patent
Hernandez et al.

(10) Patent No.: US 7,835,529 B2
(45) Date of Patent: Nov. 16, 2010

(54) SOUND CANCELING SYSTEMS AND METHODS

(75) Inventors: Walter C. Hernandez, Potomac, MD (US); Mathieu Kemp, Durham, NC (US); Frederick Vosburgh, Durham, NC (US)

(73) Assignee: Irobot Corporation, Bedford, MA (US)

( * ) Notice: Subject to any disclaimer, the term of this patent is extended or adjusted under 35 U.S.C. 154(b) by 1803 days.

(21) Appl. No.: 10/802,388

(22) Filed: Mar. 17, 2004

(65) Prior Publication Data

US 2004/0234080 A1 Nov. 25, 2004

Related U.S. Application Data

(60) Provisional application No. 60/455,745, filed on Mar. 19, 2003, provisional application No. 60/478,118, filed on Jun. 12, 2003.

(51) Int. Cl.
*G10K 11/16* (2006.01)
*A61F 11/06* (2006.01)

(52) U.S. Cl. .................... 381/71.2; 381/71.8; 381/71.6; 381/71.9; 381/71.11

(58) Field of Classification Search ................ 381/71.1, 381/71.11, 77, 71.2, 71.6, 71.8, 71.9; 600/586, 600/590
See application file for complete search history.

(56) References Cited

U.S. PATENT DOCUMENTS

| | | | | |
|---|---|---|---|---|
| 4,677,676 | A * | 6/1987 | Eriksson | 381/71.11 |
| 5,199,424 | A * | 4/1993 | Sullivan et al. | 128/204.18 |
| 5,305,587 | A | 4/1994 | Johnson | 56/16.9 |
| 5,444,786 | A | 8/1995 | Raviv | 381/71 |
| 5,844,996 | A | 12/1998 | Enzmann et al. | 381/116 |
| 6,330,336 | B1 | 12/2001 | Kasama | 381/71.1 |
| 6,368,287 | B1 | 4/2002 | Hadas | 600/529 |
| 6,436,057 | B1 * | 8/2002 | Goldsmith et al. | 600/586 |
| 6,665,410 | B1 * | 12/2003 | Parkins | 381/71.1 |
| 2001/0012368 | A1 * | 8/2001 | Yamazaki | 381/17 |

* cited by examiner

*Primary Examiner*—Vivian Chin
*Assistant Examiner*—George Monikang
(74) *Attorney, Agent, or Firm*—Myers Bigel Sibley & Sajovec

(57) ABSTRACT

A system for sound cancellation includes a source microphone for detecting sound and a speaker for broadcasting a canceling sound with respect to a cancellation location. A computational module is in communication with the source microphone and the speaker. The computational module is configured to receive a signal from the source microphone, identify a cancellation signal using a predetermined adaptive filtering function responsive to acoustics of the cancellation location, and transmit a cancellation signal to the speaker.

41 Claims, 7 Drawing Sheets

M1 Acquire undesirable sounds

M2 Determine canceling signals

M3 Emit canceling sounds

SOUND CANCELING SYSTEMS AND METHODS

This application claims priority to U.S. Provisional Patent Application Ser. Nos. 60/455,745 filed Mar. 19, 2003 and 60/478,118 filed Jun. 12, 2003, the disclosures of which are hereby incorporated by reference in their entireties.

FIELD OF THE INVENTION

This invention relates generally to sound cancellation systems and methods of operation.

BACKGROUND OF THE INVENTION

A good night's sleep is vital to health and happiness, yet many people are deprived of sleep by the habitual snoring of a bed partner. Various solutions have been introduced in attempts to lessen the burden imposed on bed partners by habitual snoring. Medicines and mechanical devices are sold over the counter and the Internet. Medical remedies include surgical alteration of the soft palette and the use of breathing assist devices. Noise generators may also be used to mask snoring and make it sound less objectionable.

Various devices have been proposed to cancel, rather than mask, snoring. One such device, proposed in U.S. Pat. No. 5,444,786, uses a microphone and acoustic speaker placed immediately in front of a snorer's nose and mouth to cancel snoring at the source. However, canceling sound can propagate and be obtrusively audible to the snorer and others. A device discussed in U.S. Pat. No. 5,844,996 uses continuous feedback control to cancel snoring sounds. A microphone close to a snorer's nose and mouth records snoring sounds and speakers proximate to a bed partner broadcast snore canceling sounds that are controlled via feedback determining microphones adhesively taped to the face of the bed partner. U.S. Pat. No. 6,368,287 discusses a face adherent device for sleep apnea screening that comprises a microphone, processor and battery in a device that is adhesively attached beneath the nose to record respiration signals. Attaching devices to the face can be physically discomforting to the snorer as well as psychologically obtrusive to snorer and bed partner alike, leading to reduced patient compliance.

Methods of canceling sound without feedback control have been implemented where the positions of source and the outlet of sound are close together and fixed, such as in U.S. Pat. No. 6,330,336, which proposes co-emitted anti-phase noise used in a photocopier to cancels the sound of an internal fan. In another example, noise-canceling earphones proposed in U.S. Pat. No. 5,305,587 detect environmental noise and broadcast a canceling signal in a fixed relationship to the ear.

SUMMARY OF THE INVENTION

According to embodiments of the present invention, systems for sound cancellation include a source microphone for detecting sound and a speaker for broadcasting a canceling sound with respect to a cancellation location. A computational module is in communication with the source microphone and the speaker. The computational module is configured to receive a signal from the source microphone, identify a cancellation signal using a predetermined adaptive filtering function responsive to acoustics of the cancellation location, and transmit a cancellation signal to the speaker.

In this configuration, sound cancellation may be performed based on the sound received from the source microphone without requiring continuous feedback signals from the cancellation signal. Embodiments of the invention may be used to reduce sound in a desired cancellation location.

According to further embodiments of the invention, a sound input is detected. A cancellation signal is identified for the sound input with respect to a cancellation location using a predetermined adaptive filtering function. A cancellation sound is broadcast for canceling sound proximate the cancellation location.

In some embodiments, a first sound is detected at a first location and a modified second sound is detected at a second location. The modified second sound is a result of sound propagating to the second location. An adaptive filtering function can be determined that approximates the second sound from the first sound. A cancellation signal proximate the second location can be determined from the first sound and the adaptive filtering function without requiring substantially continuous feedback from the second location.

In some embodiments, methods for canceling sound include detecting a first sound at a first location and detecting a modified second sound at a second location. The modified second sound is the result of sound propagating to the second location. An adaptive filtering function can be determined to approximate the second modified sound from the first sound.

Further embodiments of the invention provide a microphone spatially remote from a subject. A sound input to the microphone is analyzed for indications of a health condition comprising at least one of: sleep apnea, pulmonary congestion, pulmonary edema, asthma, halted breathing, abnormal breathing, arousal, and disturbed sleep.

In some embodiments, systems for sound cancellation include a source microphone for detecting sound and a parametric speaker configured to transmit a cancellation sound that is localized with respect to a cancellation location. In other embodiments, methods for canceling sound include detecting a sound and transmitting a canceling signal from a parametric speaker that locally cancels the sound with respect to a cancellation location.

DETAILED DESCRIPTION

Figure 1:
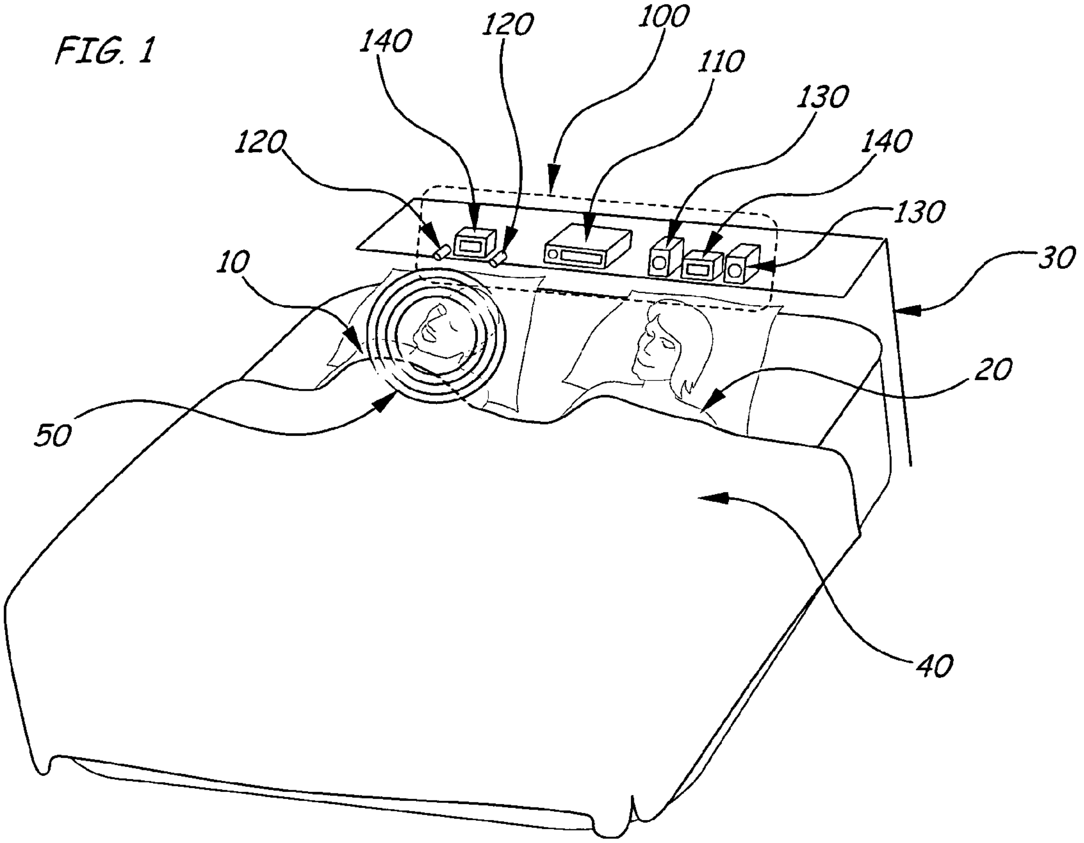
FIG. 1 is a schematic illustration of a system according to embodiments of the present invention in use on the headboard of a bed in which a snorer and a bed partner are sleeping.

The present invention now will be described more fully hereinafter with reference to the accompanying drawings, in which various embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals in the drawings denote like members.

Embodiments of the present invention include devices and methods for detecting, analyzing, and canceling sounds. In some embodiments, noise cancellation can be provided without requiring continuous acoustic feedback control. For example, an adaptive filtering function can be determined by detecting sound at a source microphone, detecting sound at the location at which sound cancellation is desired, and comparing the sound at the microphone with the sound at the cancellation location. A function may be determined that identifies an approximation of the sound transformation between the sound detected at the microphone and the sound at the cancellation location. Once the adaptive filtering function has been determined, a cancellation sound may be broadcast responsive to the sound detected at the source microphone without requiring additional feedback from the cancellation location.

Certain embodiments may be useful for canceling snoring sounds with respect to the bed partner of a snorer; however, embodiments of the invention may be applied to other sounds that are intrusive to a person, asleep or awake. While described herein with respect to the cancellation of snoring sounds, embodiments of the invention can be used to cancel a wide range of undesirable sounds, such as from an entertainment system, or mechanical or electrical devices.

Certain embodiments of the invention may analyze sound to determine if a change in respiratory sounds occurs sufficient to indicate a health condition such as sleep apnea, pulmonary congestion, pulmonary edema, asthma, halted breathing, abnormal breathing, arousal, and disturbed sleep. In some embodiments, parametric (ultrasound) speakers may be used to cancel sound.

Devices according to embodiments of the invention may be unobtrusive and low in cost, using adaptive signal processing techniques with non-contact sensors and emitters to accomplish various tasks that can include: 1) determining the origin and characteristics of snoring sound, 2) determining a space having reduced noise or a “cancellation location” or “cancellation space” where canceling the sound of snoring is desirable (e.g., at the ear of a bed partner), 3) determining propagation-related modifications of snoring sound reaching a bed partner’s ears, 4) projecting a canceling sound to create space with reduced noise in which the sound of snoring is substantially cancelled, 5) maintaining the position of the cancellation space with respect to the position of ears of bed partner, 6) analyzing characteristics of snoring sound, 7) and issuing an alarm or other communication when analysis indicates a condition possibly warranting medical attention or analysis.

In applications related to snoring, embodiments of the invention can include a computer module for processing signals and algorithms, non-contact acoustic microphones to detect sounds and produce signals for processing, acoustic speakers for projecting canceling sounds, and, in certain embodiments, sensors for locating the position of the bed partner and the snorer. In certain embodiments, a plurality of speakers can be used to produce a statically positioned enhanced cancellation space which may be created covering all or most positions that a bed partner’s head can be expected to occupy during a night’s sleep. In other embodiments, a cancellation space or enhanced cancellation location is adaptively positioned to maintain spatial correspondence of canceling with respect to the ears of the bed partner.

Embodiments of the invention can provide a bed partner or a snoring individual with sleep-conducive quiet while providing capabilities for detecting indications and issuing alarms related to distressed sleep or possible medical condition, which may require timely attention.

Embodiments of the invention can include components for detecting, processing, and projecting acoustic signals or sounds. Various techniques can be used for providing the canceling of sounds, such as snoring, with respect to fixed or movably controlled positions in space as a means of providing a substantially snore-free perceptual environment for an individual sharing a bed or room with someone who snores.

A cancellation space may be provided in a range of size and degree of enhancement. In certain embodiments implementing a cancellation space at static positions, a larger volume cancellation space may be created to enable a sleeping person to move during sleep, yet still enjoy benefits of snore canceling without continuous acoustic feedback control signals from intrusive devices.

FIG. 1 depicts embodiments according to the invention including a system 100 that can (optionally) sense a position of the snorer 10 or the bed partner 20. The system 100 includes components placed conveniently, e.g., on a headboard 30 of a bed 40, to provide canceling of the snoring sounds 50. The system 100 includes a base unit 110, microphones 120, audio speakers 130, and, optionally, locating components 140. In certain embodiments, locating components can be omitted.

As illustrated, the system 100 includes two microphones 120; however, one, two or more microphones may be used. Microphone signals are provided to the base unit 110 by wired or wireless techniques. Microphone signals may be conditioned and digitized before being provided to the base unit 110. Microphone signals may also be conditioned and digitized in the base unit 110.

The base unit 110 can include a computational module that is in communication with the microphones 120 and the speakers 130. The computational module receives a signal from the microphones 120, identifies a cancellation signal using a predetermined adaptive filtering function responsive to the acoustics proximate the bed partner 20, and transmits a cancellation signal to the speaker 120. The adaptive filtering function can determine an approximate sound transformation at a specified location without requiring continuous feedback from the location in which cancellation is desired. The adaptive filtering function can be determined by receiving a sound input from the microphone 120, receiving another sound input from the cancellation location (e.g., near the bed partner 20), and determining a function adaptive to the sound transformation between the sound input from the microphone 120 and the sound input from the cancellation location. The transformation can include adaptation to changes in acoustics such as sound velocity, as affected by room temperature. For example, a sound velocity and/or thermometer can be provided, and the adaptive filtering function can use the sound velocity and/or thermometer readings to determine the sound transformation between the sound input and the cancellation location. Once an adaptive filtering function has been determined, sound input from the cancellation location may not be required in order to produce the desired sound canceling signals. If acoustic changes in a room occur (e.g., through movement of objects, changes in location of sound sources, etc.), a new adaptive filtering function may be needed. The adaptive filtering function may take into account the position of the bed partner 20 and/or the position of the snorer 10.

Figure 2:
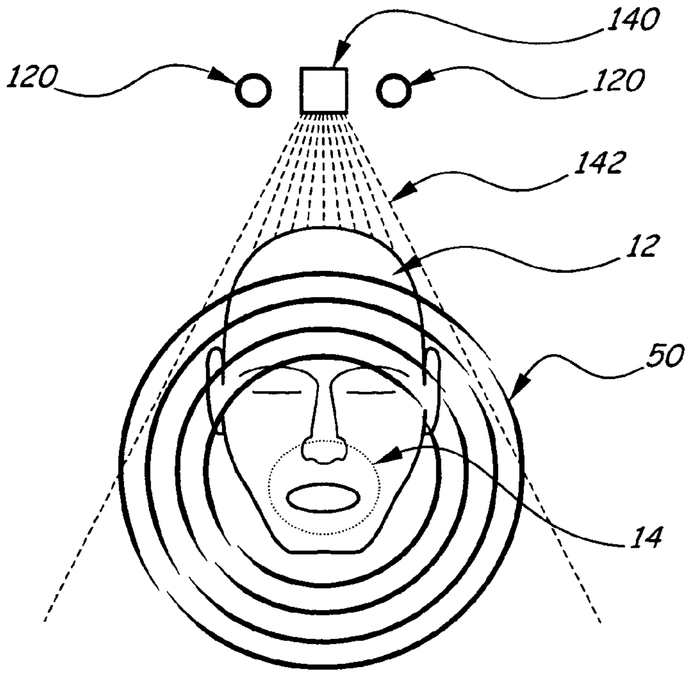
FIG. 2 is a schematic illustration of two microphones detecting the snoring sound and a position detector determining a head position of the snorer according to embodiments of the present invention.

Referring to FIG. 2, microphones 120 for detecting the snoring sound 50 can be placed in various positions and at various distances from the snorer 10, although a distance of approximately one foot from the snorer's head 12 is desirable when the system 100 is employed by two persons sharing one bed 40. Longer distances are acceptable when interpersonal distance is greater, e.g., if the snorer 10 and the bed partner 20 occupy a large bed 40 or separate beds 40. It is further desirable, although not required, that microphones 120 remain in a more or less constant position from night to night.

The optional locating component 140 can be used to determine the position of the snorer 10, the head 22, and/or the buccal-nasal region ("BNR") 14. Microphones 120 can be used to locate the position of the sound source or the BNR 14. The locating component 140 can be a locating sensor, such as a locating sensor available commercially from Canesta Inc., which projects a plurality of pulsed infrared light beams 142, return times of which can be used to determine distances to various points on the snorer head 12 to locate the position of the BNR 14, or to various points on the bed partner head 22 to locate the position of the ears 24. The locating component 140 can utilize other signals such as other optical, ultrasonic, acoustic, electromagnetic, or impedance signals. Any suitable locating component can be used for the locating component 140. Signals acquired by the microphone 120 can be used for locating the BNR 14 to replace or complement the functions of the locating component 140. For example, a plurality of microphone signals may be subject to multichannel processing methods such as beam forming to the BNR 14.

Figure 3A:
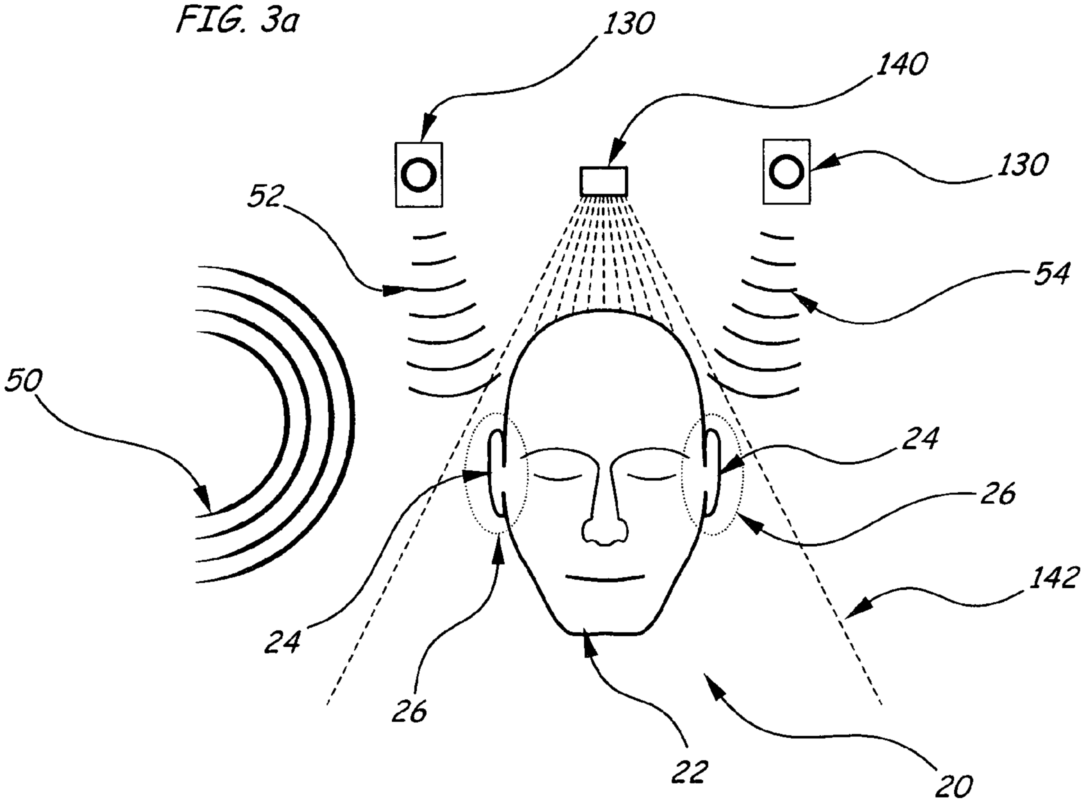
FIG. 3*a* is a schematic illustration of two speakers broadcasting canceling sound to create cancellation spaces associated with a bed partner's ears and an optical locating device determining the position of the bed partner according to embodiments of the present invention.

Referring to FIG. 3*a*, which depicts the bed partner 20, the speakers 130 may be placed reasonably proximate to the bed partner head 22, for example, at a distance of about one foot. The speakers 130 may produce a cancellation space 26 with respect to the ears 24 of the bed partner 20. In embodiments including a plurality of speakers 130, a speaker 130 placed closer to the snorer 10 than midline of the bed partner head 22 can be used primarily to produce near-ear canceling sound 52 (i.e., sounds that are near the ear that is nearest the sound source) and a speaker 130 further from the snorer can be used primarily to produce far-ear canceling sound 54 (i.e., sounds that are near the ear that is furthest from the sound source). Near-ear canceling sound 52 and far-ear canceling sounds 54 may be equivalent, or near-ear canceling sound 52 and far-ear canceling sounds 54 may be different. Various placements of the speakers 130 may be suitable. Preferably, the combined distance between the speaker 130 and the corresponding ear 24 and between the microphone 120 and the BNR 14 is less than the distance between the ear 24 and the BNR 14. Microphones 120 may be placed to detect breathing sounds from the bed partner 20, which may be used to locate the position of the snorer 10 or for health condition screening purposes.

Figure 3B:
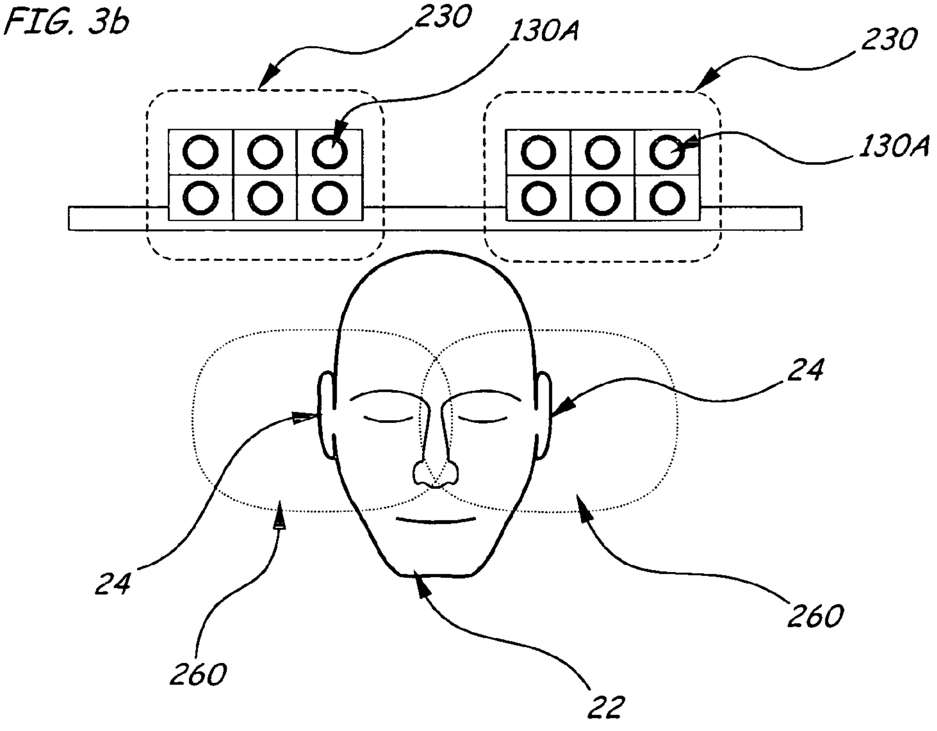
FIG. 3*b* is a schematic illustration of an array of speakers broadcasting canceling sound to create an enhanced cancellation space without using a locating device according to embodiments of the present invention.

FIG. 3*b* depicts a plurality of speakers 130A, including two speaker arrays 230A, that can be used to create enhanced cancellation spaces 260, which can be larger or otherwise enhanced with respect to the cancellation space 26 created with one speaker 130 (in FIG. 3*a*). The enhanced cancellation space 260 may be sufficiently large that the bed partner 20 can move while asleep yet retain benefits of snore canceling. In some embodiments, the enhanced cancellation space 260 may be maintained without resort to continuous acoustic feedback control, or information from the position component 140. An adaptive filtering function for transforming sound from the microphone 120 (FIG. 1) to a cancellation space 260 to account for acoustics and sound propagation characteristics can be used, for example, by a computational module in the base unit 110 to determine an appropriate cancellation signal. A training period may be used in order to derive an adaptive filtering function appropriate for the particular acoustics of a room. The training period can include detecting sound at the microphones 120 and in the location in which cancellation is desired such as the cancellation space 260. A function can then be determined that approximates the transformation of the sound that occurs between the two locations. The function can further include "cross-talk" cancellation features to reduce feedback, e.g., the effects of canceling sounds 52, 54 that may also be detected by the microphone 120. After the training period, the snorer sound 50 can be cancelled in the cancellation space 260 without requiring continuing sound input from the cancellation space 260.

Figure 3C:
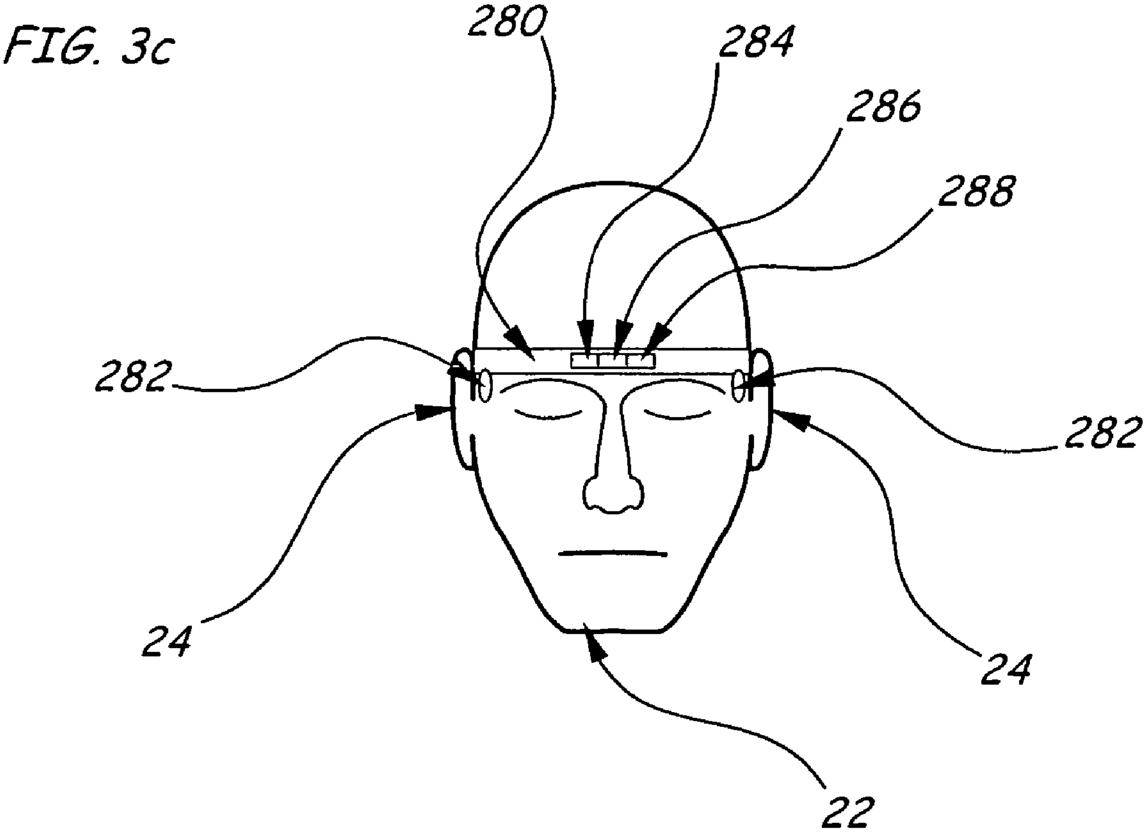
FIG. 3*c* is a schematic illustration of a training headband worn by a bed partner during algorithm training period according to embodiments of the present invention.

FIG. 3*c* depicts a headband 280 that can be worn by the bed partner 20 during an algorithm training period to determine an adaptive filtering function for canceling sound near the location of the headband 280 during the training period. Algorithm training can include calculation of the snore canceling signal modified coefficients, including modifications owing to changes in sound during propagation between the snorer 10 and the bed partner 20. When the headband 280 is in place, the microphones 282 preferably lie in close proximity to the bed partner ears 24. The headband 280 can additionally include electronics 284, a power supply 286, and wireless communicating means 288, although a tether conducting power or data can be used for providing power and/or communications to the headband 280.

Figure 3D:
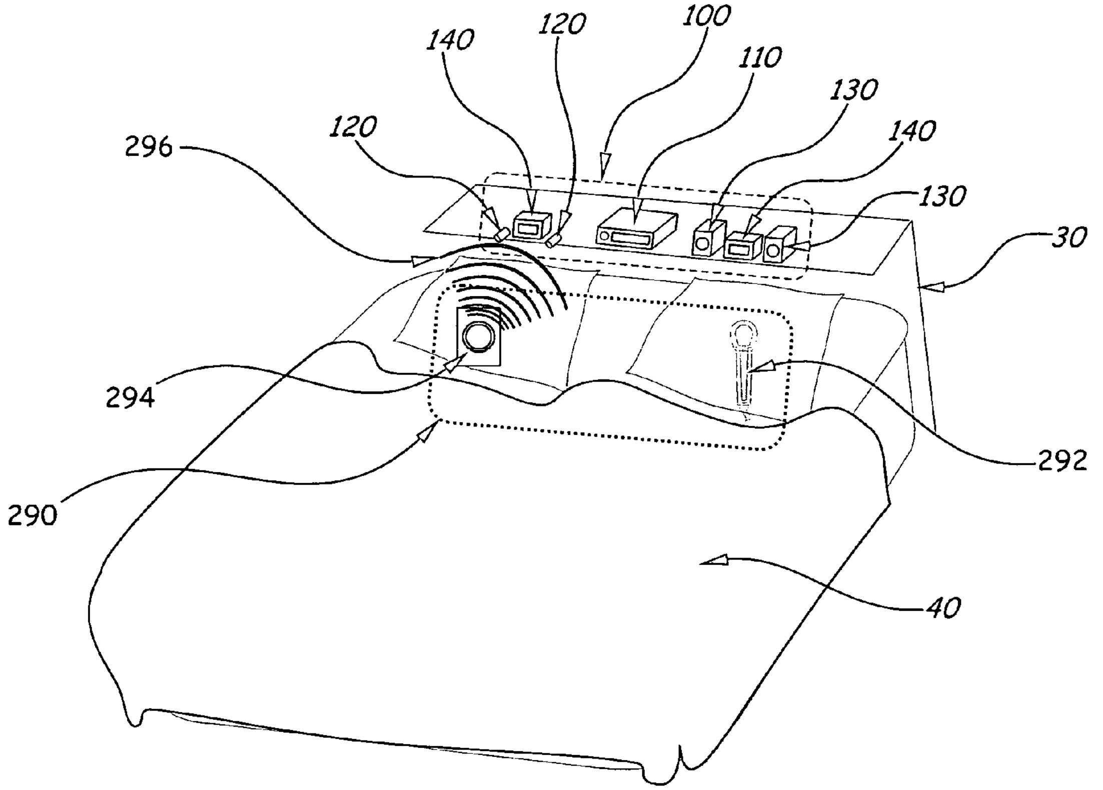
FIG. 3*d* is a schematic illustration of a training system that does not requiring the snorer or the bed partner to be present according to embodiments of the present invention.

FIG. 3*d* depicts an algorithm training system 290 that can be used in certain embodiments (for example, before a couple retires to bed). Algorithm training using a pre-retirement training system 290 can be as a complement or alternative to training using the headband 280. Training system 290 can include at least one training microphone 292. It can optionally also include at least one training speaker 292. The training microphone 292 and the training speaker 294 can be placed, respectively, at locations representative of those expected during the night of the bed partner ear 24 and of the snorer buccal-nasal region 14. Pre-retirement training can replace or supplement training using the headband 280.

The training system 290 can be used without the snorer or the bed partner present. The training microphone 292 can be used without the training speaker 294 while the snorer is in the bed 30 emitting snore sounds or other sounds, e.g., with or without the bed partner or a training headband being present. A training headband, such as headband 280 in FIG. 3*c*, can be used instead of the training microphone 292. The bed partner can conduct algorithm training in the bed 30 using the headband 280 and the training speaker 294 without requiring that the snorer be present.

The training microphone 292 and the training speaker 294 can be mounted in geometric objects that may resemble the human head. The training microphone 292 can be mounted on the lateral aspect of such a geometric object mimicking location of an ear 24. The training speaker 294 can be mounted on a frontal aspect of such an object to mimic location of the buccal-nasal region of the human head. Geometric objects can have sound interactive characteristics somewhat similar to those of the human head. An object can further resemble a human head, such as by having a partial covering of simulated hair or protuberances resembling a sleeper's ears, nose, eyes, mouth, neck, or torso.

During a training session, the training speaker 294 can emit a calibration sound 296 that may have known characteristics. Known characteristics can be reflective of a sound for which cancellation is desired, e.g., snoring. A training sound may or may not sound to the ear like the sound to be cancelled. One training sound can be a plurality of chirps comprising a bandwidth containing frequencies representative of sleep breathing sounds. In the case of the snore sound 50, one such bandwidth can be 50 Hz to 1 kHz, although many other bandwidths are acceptable. Other types of sound, such as recorded or live speech, or other wide band signals having a central frequency within the range of snoring frequencies, can also be used as a training sound.

Figure 4A:
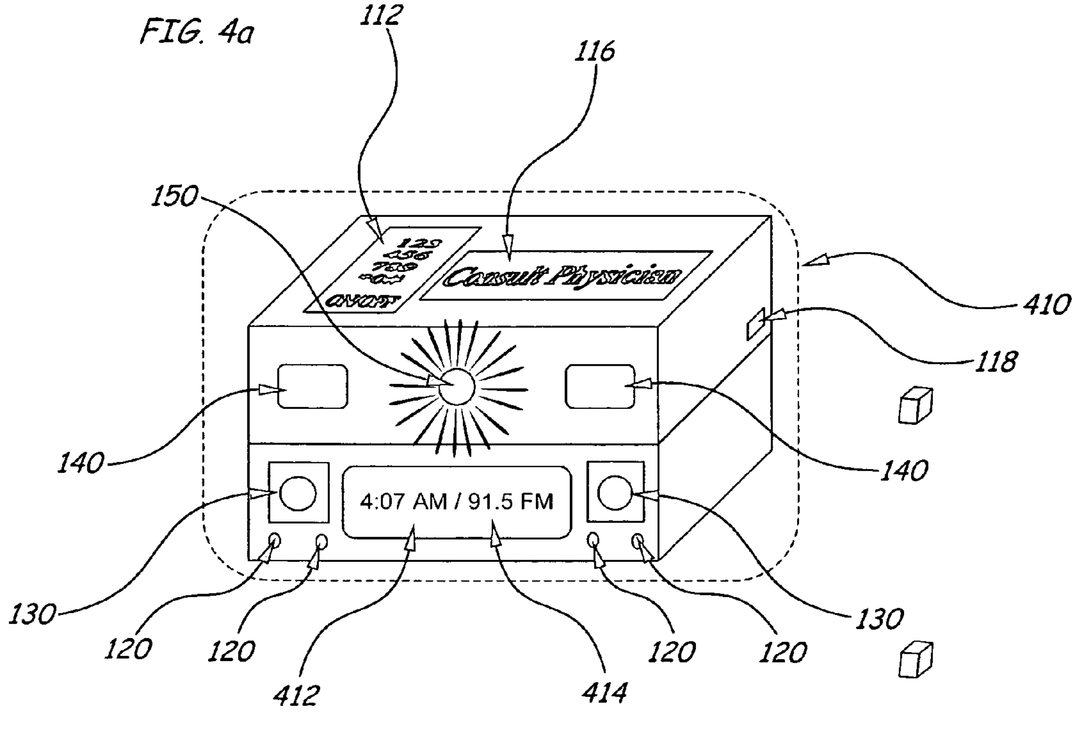
FIG. 4*a* is a schematic illustration of an integrated snore canceling device having additional components for time display and radio broadcast according to embodiments of the present invention.

FIG. 4*a* depicts an integrated device 410 according to embodiments of the invention. The integrated device 410 can include components for audio entertainment, e.g., a radio tuner 412, and a time display 414. The device 410 can include microphones 420, speakers 430, and a locating component 440. The device 410 can include a light display 150 for alerting a user if sounds are detected that indicate a health condition, such as sleep apnea, pulmonary edema, or interrupted or otherwise distressed breathing or sleep. A display 116 can also be provided, for example, to inform a user that he or she should consult a physician if a medical condition is detected. A touchpad 112 and/or a phone line 118 can also be provided. Data from the device 410 can be transferred to a third party over the phone line 118 or other suitable communications connections, such as an Internet connection or wireless connection. The user can control the device 410 by entering commands to the touchpad 112, for example, to control the collection of data and/or communications with a third party.

In some embodiments, the integrated device 410 can be used to listen to a radio broadcast with snore canceling to enhance hearing of the broadcast. Additionally, the integrated device 410 can be used for entertainment, sound canceling, and/or sound analysis purposes. Furthermore, certain embodiments can include a television tuner, DVD player, telephone, or other source of audio that the bed partner 20 desires to hear without interference from the snoring sound 50.

Figures 4B, 5A:
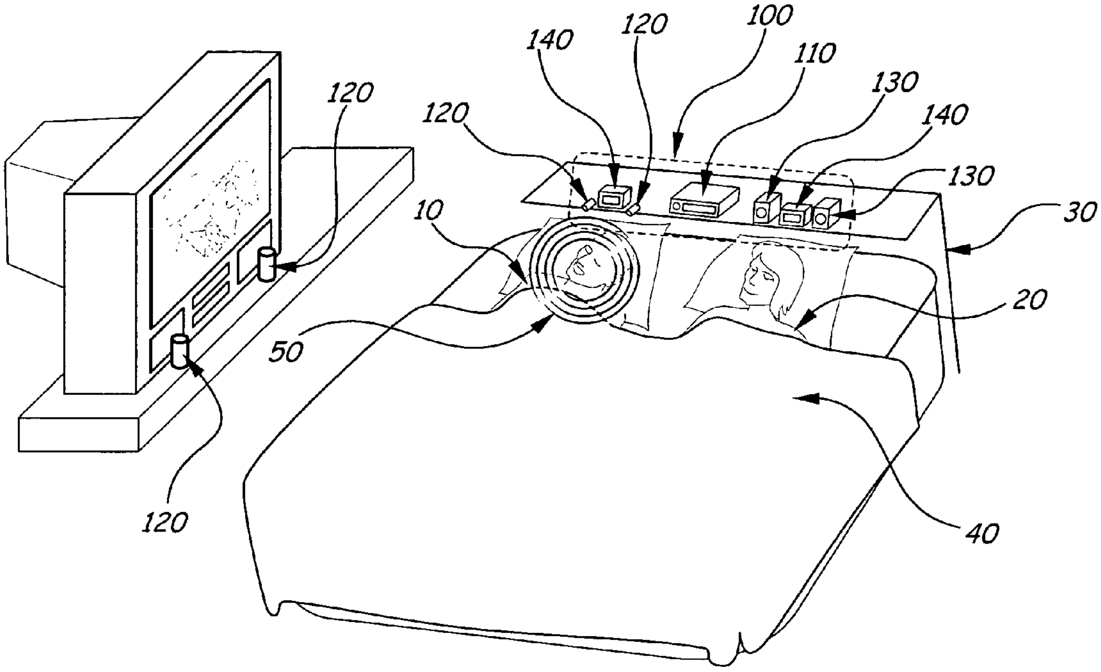
FIG. 4*b* is a schematic illustration of a device that can cancel sounds from a snorer and a television according to embodiments of the present invention.
FIG. 5*a* is a block diagram illustrating operations according to embodiments of the present invention.

Referring to FIG. 4*b*, a system 100 can include microphones 120 for detecting other undesirable sound, such as from a television 450. Other undesirable sounds may include sounds from a compressor, fan, pump, or other electrical or mechanical device in the acoustic environment. The computational module in the base unit 110 can include an adaptive filtering function for receiving such sounds and for providing a signal to cancel the undesirable sounds beneficially for the bed partner 20. In such applications, microphones 120 can be placed in reasonable proximity to source of the undesirable sound and preferably along the general path of propagation to the bed partner 20. Such other sound canceling can be used separately or together with the microphones 120 primarily to detect snoring sounds 50 to enable combinations of canceling that may result in a more peaceable sleep environment. Canceling of other sounds such as a television 450 or electrical or mechanical device can be provided for snorer 10 as described herein.

Referring to FIG. 5*a*, snoring sounds are acquired (Block M1), e.g., by microphones 120, canceling signals are determined (Block M2), e.g., by the computational module in the base unit 110, and canceling sounds (Block M3) are emitted, e.g., by the speakers 130. Determination of the canceling signals (Block M3) can include multi-sensor processing methods such as cross-talk removal to reduce effects of canceling sounds being detected by the snoring microphone 120. Although the following discussion is in terms of one ear, it should be understood that systems and methods according to embodiments of the present invention may be applied to either or both ears or any spatial region.

Figure 5B:
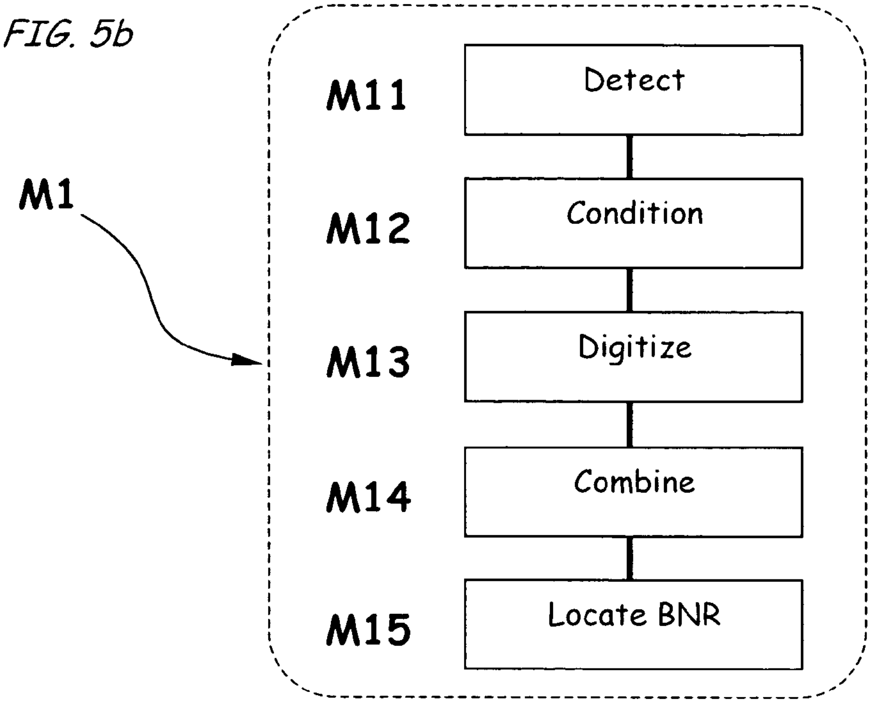
FIG. 5*b* is a block diagram illustrating operations according to embodiments of the present invention.
Figure 5C:
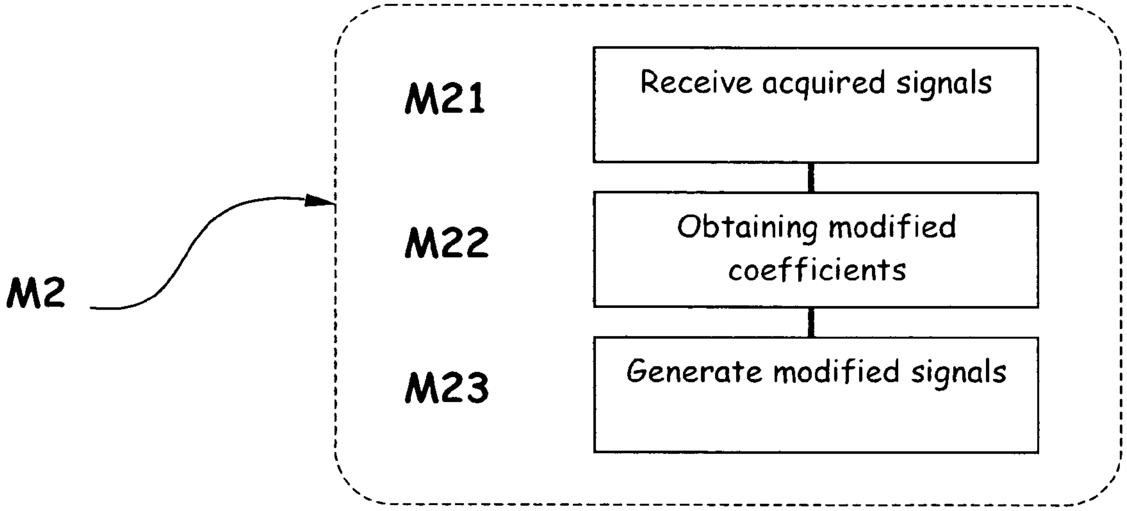
FIG. 5*c* is a block diagram illustrating operations according to embodiments of the present invention.
Figure 5D:
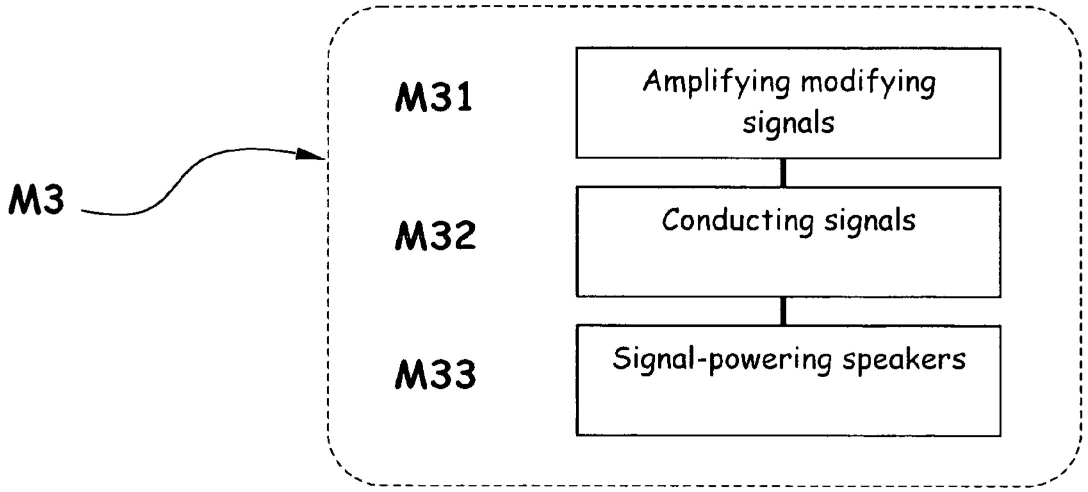
FIG. 5*d* is a block diagram illustrating operations according to embodiments of the present invention.

As shown in FIG. 5*b*, Block M1 can include detecting signals (Block M11), conditioning signals (Block M12), digitizing signals (Block M13), and, for embodiments using more than one microphone 120, combining signals (Block M14), e.g., by beam forming, to yield an enhanced signal and, optionally, to determine a position of the sound source, such as the position of the BNR 14 (Block M15). Digital signals may be provided for the operations of Block M2. As depicted in FIG. 5*c*, Block M2 can include receiving acquired signals (Block M21), obtaining modifying coefficients (Block M22), and generating modified signals (Block M23). As depicted in FIG. 5*d*, Block M3 can include amplifying modified signals (Block M31), conducting signals to the speaker 130 (Block 32), and powering the speakers 130 (Block M33).

Figure 5E:
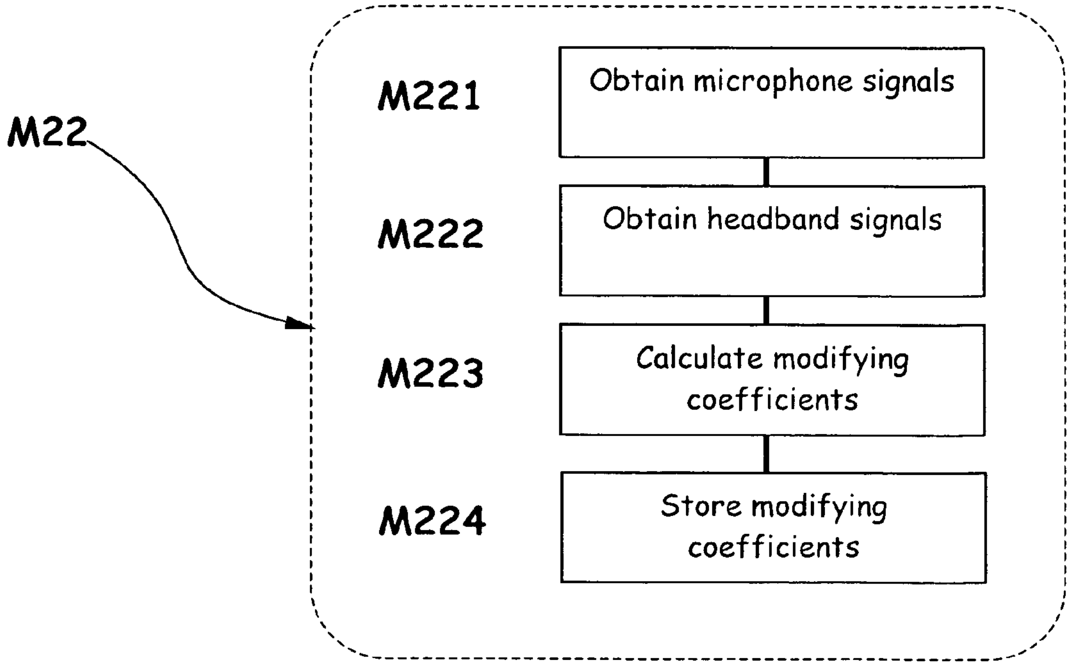
FIG. 5*e* is a block diagram illustrating operations according to embodiments of the present invention.

FIG. 5*e* describes an exemplary algorithm training session for determining modified coefficients in Block M22. Microphone signals are obtained, e.g., from microphones 120 (Block M221). Signals are then obtained from a training device such as the headband 280 in FIG. 3*c* placed in the location in which sound cancellation is desired (Block M222). Modified coefficients are calculated to approximate the sound transformation between the microphone signals and the training device (headband) signals (Block M223). Modified coefficients may be stored in memory, e.g., in the base unit 110 (Block M224). The coefficients can account for propagation effects to determine a cancellation signal, for example, using an adaptive filtering function. Modifications of the snoring sound 50 taken into account by the modified coefficients can include phase, attenuation, and reverberation effects.

A plurality of modified coefficients can be represented by a matrix W representing a situational transfer function. Calculating the modified coefficients (Block M223) for the situational transfer function W can employ various methods. For example, the difference between a power function of the snore sound 50 and the canceling sound 52,54 detectable more or less simultaneously at the ear 24 for a plurality of audible frequencies may be minimized. This can be accomplished by time-domain or frequency-domain techniques. Preferably W is determined with respect to snoring frequencies, which commonly are predominantly below 500 Hz.

An example of a technique that can be used to minimize differences in power employs the statistical method known as a least squares estimator ("LSE") to determine coefficients in W that minimize difference. It should be understood that other techniques can be used to determine coefficients in W, including mathematical techniques known to those of skill in the art. An LSE can be used to computationally determine one or more sets of coefficients providing a desirable level of canceling. In certain embodiments, the desirable level of canceling is reached when one or more convergence criteria are met, e.g., reduction of between about 98% to about 80%, or between about 99.9% to about 50% of the power of snoring sounds 50 below 500 Hz.

Another method of calculating W is to determine and combine transfer functions for propagation among the BNR 12, microphones 120, and speakers 130. It can be shown that a desirable form of W is of the form:

$$W=1/(d-c*e)$$

where c can represent a transfer function for sound propagation from the snorer 10 to the microphone 120, e can represent a transfer function for propagation from the speaker 130 to the bed partner 20, and d can represent a transfer function for propagation from the microphone 120 to the speaker 130. The * operator denotes mathematical convolution. W or a plurality of individual transfer functions, e.g., c, d, and e, can be determined by time-domain or frequency-domain methods in the various embodiments. In certain embodiments employing a plurality of microphones 120 or speakers 130, W, c, d, and e can be in the form of a matrix.

Referring to FIGS. 1 and 5*b*, detecting sound from the microphones 120 (Block M11) is preferably conducted with a plurality of the microphones 120 placed in reasonable proximity to the snorer 10 so that the path length of the snore sound 50 to the microphone 120 plus the path length from the speaker 130 to the bed partner ears 24 is less than the length of the propagation path directly from the snorer 10 to the bed partner's ears 24. Greater separation between the NBR 14 and the bed partner 20 may afford greater freedom in the placement of the sensor 120. In this configuration, the cancellation sound may reach the ears 24 prior to the direct propagation between the NBR 14 to the ears 24.

In acquiring signals, conditioning (Block M12) can be conducted by such methods as filtering and pre-amplifying. Conditioned signals then can be converted to digital signals by digital sampling using an analog-to-digital converter. The digital signals may be processed by various means, which can include; 1) multi-sensor processing for embodiments utilizing signals from a plurality of microphones 24, 2) time-frequency conversion and parameter deriving useful in characterizing detected snoring sound 50, 3) time domain processing such as by wavelet or least squares methods or other convergence methods to determine a plurality of coefficients representative of snoring sound 50, 4) coefficient modifying to adjust for various position and propagation effects on snoring sound 50 detectable at the bed partner's ears 24, and producing an output signal to drive speakers to produce the desired canceling sound to substantially eliminate the sound of snoring at the ears of bed partner's.

Referring to FIG. 5*c*, obtaining modified coefficients at Block M22 can include retrieving coefficients placed in memory during algorithm training. Such coefficients can reflect effects of the position of the snorer 10 or the BNR 14, or the bed partner 20 or the ears 24 (FIG. 1). A change in position of the snorer 10 or the bed partner 20 can alter snoring sound reaching the bed partner's ears 24. Such alterations can include alterations in power, spectral character, and reverberation pattern. Modified coefficients can provide adjustments for such effects in various ways.

For embodiments in which positional information for the bed partner 20 is not used, modified coefficients can reflect values determined for various positions and conditions that alter sound propagation; as such, modified coefficients are representative coefficients that provide a level of canceling for situations where positional information is not used. With information regarding the position of the bed partner 20, modified coefficients can be enhanced to provide a larger cancellation space or region. In embodiments where positional information regarding the snorer 10 and the bed partner 20 is used, canceling can be further enhanced.

Spatial volumes, such as cancellation space 26 (FIG. 3*a*), may be provided in which undesirable sound, such as snoring sound 50, is reduced, as perceived by bed partner 20. The cancellation space 26 may be created in a fixed-spatial position that can result in substantially snore-free hearing. The cancellation space 26 created by a single speaker 130 can be relatively small, having dimensions depending in part on wave-length components of the snoring sound 50.

The bed partner 20 may perceive loss of canceling as a result of moving the ears 24 out of the cancellation space 26. Therefore, a plurality of speakers 130 may be employed, such as a speaker array 230, to create an enhanced cancellation space 260 (FIG. 3*b*) including a greater spatial volume, enabling normal sleep movements while retaining benefit of canceling. In certain embodiments, W differs somewhat among the speakers 130, for example, to account for differences in propagation distance from each speaker 130 to the bed partner's ear 24.

The cancellation space 26 can be produced without information regarding the current position of the snorer 10 or the bed partner 20. In such embodiments, robust canceling can be provided with respect to affects of changes in position of the snorer 10 or the bed partner 20, such as can occur during sleep by various means. That is, sound cancellation may be provided despite some changes in the position of the snorer 10 or the bed partner 20. The cancellation space 26 associated with one ear 24 can abut or overlap the cancellation space 26 associated with a second ear 24, creating a single, continuous cancellation space 260 extending beyond the expected range of movement of the bed partner ears 24 during a night's sleep. In certain other embodiments, a formulation of W robust with respect to changes in the position of the snorer 10 or the bed partner 20 can be used.

Additional information, such as from the locating component 140, can be used. Such additional information can include the positional information regarding the bed partner 20, or the head 22 or the ears 24 thereof, or the snorer 10, the head 12 of the snorer or the BNR 14. A plurality of microphones 120 can be used to provide positional information by various methods, including multi-sensor processing, time lag determinations, coherence determinations or triangulation.

In certain embodiments, the positional information regarding the snorer 10 and the bed partner 20 can be used to adapt canceling to changes in the snoring sound 50 incident at the bed partner's ears 24 resulting from such movement. Examples of such alterations can include changes in power, frequency content, time delay, or reverberation pattern. Canceling may be adapted to account for movement of the bed partner 20 by tracking such movement, for example with a locating component 140, and correspondingly adjusting position of the cancellation space 26. In certain alternative embodiments, canceling may be adapted to movements of the snorer by adjustments evidenced in such canceling parameters as power, spectral content, time delay, and reverberation pattern.

Continuous feedback control may be replaced with canceling in spatial volumes at static or movably controlled positions in 3D space based on self-training algorithm methods. FIG. 5*e* illustrates algorithm training, which includes obtaining signals from microphones 120 (Block M221), obtaining signals from training microphones such as from the training microphones 282 (Block M222), and determining coefficients providing canceling of the snoring sound 50 (Block M223). Training may be conducted without information regarding the position of the snorer 10 or the bed partner 20 (FIG. 1). In such embodiments, a cancellation space 24 (FIG. 3*a*) can be created at a predetermined position or cancellation location. In embodiments employing information regarding the bed partner position, coefficients can be produced that reflect such position and can control position of cancellation space 26. Position control can be used to maintain coinciding position of ears 24 and cancellation space 26.

In embodiments where the position of the snorer 10 (FIG. 1) is not determined, coefficients can be determined that reflect the position and pattern of movement of the snorer 10 or the BNR 14 that occur during algorithm training period. When the position of the snorer 10 is employed, coefficients can be produced to provide enhanced canceling. Once coefficients are determined and modified during a training session they can remain constant until additional training is desirably undertaken. Such additional training can be undertaken subsequent to changes in the acoustic environment that adversely affect canceling.

Snoring sound can be analyzed to screen for audible patterns consistent with a medical condition, for example, sleep apnea, pulmonary edema, or interrupted or otherwise distressed breathing or sleep. Analysis can be conducted with a single microphone 24, although using signals from a plurality of microphones 24 to produce an enhanced signal, e.g., by beam forming, that is isolated from background noise and can better support analysis. Moreover, sleeping sounds from more than one subject may be detected simultaneously and then isolated as separate sounds so that the sounds from each individual subject may be analyzed. Sound from the snorer may also be isolated by tracking the location of the snorer. Analyzing sound for health-related conditions can include calculating time-domain or frequency-domain parameters, e.g., using time domain methods such as wavelets or frequency domain methods such as spectral analysis, and comparing calculated parameters to ones indicative of various medical conditions. When analysis indicates a pattern reasonably consistent with a medical condition, or distressed breathing or sleeping, an alarm or other information can be communicated. Screening the sound may be conducted while the sound is cancelled. Screening or canceling the sound can be conducted independently.

An alarm can be communicated with a flashing light, an audible signal, a displayed message, or by communication to another device such as a central monitoring station or to an individual such as a relative or medical provider. Messages can include: an indication of a possible medical condition, a recommendation to consult a health care provider, or a recommendation that data be sent for analysis by a previously designated individual whose contact information is provided to the device. In an alternative embodiment, a user can direct that data be sent by pressing a button or, referring to FIG. 4*a*, appropriate area of a touchpad 112, with communication then being conducted via the phone line 118. An Internet connection, removable data storage, or wireless components can also be used to communicate data to a third party. Communicated data can included recorded snoring sounds 50, results of analyzing such sounds, and time and activity data related to the snorer 10 or the bed partner 20.

Additional data can be included in such communications. Such additional data can include stored individual medical information, or output from other monitoring sensors, e.g., blood pressure monitor, pulse oximeter, EKG, temperature, or blood velocity. Such additional data can be entered by a user or obtained from other devices by wired, wireless, or removable memory means, or from other sensors comprising components in an integrated device 410.

In certain embodiments, snoring sound signals and parameters are stored for a period of time to enable communicating a plurality of such information, for example, for confirming screening analysis for health conditions. Such information can also be analyzed for other medical conditions, e.g., for lung congestion in a person with sleep apnea even if screening only is indicative of apnea.

In further embodiments according to the invention, a cancellation sound can be formed using parametric speakers. Parametric speakers emit ultrasonic signals, i.e., those normally beyond the range of human hearing, which interact with each other or with the air through which they propagate to form audible signals of limitable spatial extent. Devices emitting interacting ultrasonic signals, such as proposed in U.S. Pat. No. 6,011,855, the disclosure of which is hereby incorporated by reference in its entirety as if fully set forth herein, emit a plurality of ultrasonic signals of different frequencies that, form a difference signal within the audible range in spatial regions where the signals interact but not elsewhere. Other devices, such as discussed in U.S. Pat. No. 4,823,908 and U.S. patent Publication No. 2001/0007591 A1, the disclosures of which are hereby incorporated by reference in their entirety as if fully set forth herein, propagate a directional ultrasound signal comprising a carrier and a modulating signal. Nonlinear interaction of the directional ultrasound with the air causes demodulation, making the modulating signal audible along the propagation path but not elsewhere.

For example, the system 100 shown in FIG. 1 can include speakers 130 that are parametric. The microphone 120 can detect a sound that propagates from the snorer 10 to the bed partner 20. The speakers 130 can be parametric speakers that can each transmit a signal. The resulting combination of the ultrasonic signals produced by the transmitters can together form a canceling sound with respect to the location of the bed partner 20. The canceling sound can be focused in the location of the bed partner 20 so that the canceling sound is generally inaudible outside the transmission paths of the ultrasonic signal. In an alternative use of parametric devices, one or more speakers can project a directional ultrasound signal that is demodulated by air along its propagation path to provide a canceling sound in the audible range, e.g., with respect to the bed partner 20. For example, the ultrasonic signal produced by the parametric speaker can be a modulated ultrasonic signal comprising an ultrasonic carrier frequency component and a modulation component, which can have a normally audible frequency. Nonlinear interaction between the modulated ultrasonic signal and the air through which the signal propagates can demodulate the modulated ultrasonic signal and create a cancellation sound that is audible along the propagation path of the ultrasonic carrier frequency signal.

For example, a 100 KHz (ultrasonic) carrier frequency can be modulated by a 440 Hz (audible) signal to form a modulated signal. The resulting modulated ultrasonic signal is generally not audible. However, such a signal can be demodulated, such as by the nonlinear interaction between the signal and air. The demodulation results in a separate audible 440 Hz signal. In this example, the 440 Hz signal corresponds to the normally audible tone of “A” above middle “C” on a piano and can be a frequency component of a snoring sound.

An adaptive filtering function can be applied to the sound detected by the microphones 120 to identify a suitable canceling sound signal to be produced by the combination of ultrasonic signals. The adaptive filtering function approximates the sound propagation of the sound detected by the microphones 120 to the cancellation location, which in this application is the location of the bed partner 20.

While this invention has been particularly shown and described with reference to preferred embodiments thereof, the preferred embodiments described above are merely illustrative and are not intended to limit the scope of the invention. It will be understood by those skilled in the art that various changes in form and details may be made therein without departing from the spirit and scope of the invention as defined by the appended claims.

That which is claimed is:

1. A system for sound cancellation comprising:

a source microphone for detecting sound propagating from a mobile sound source remote from the source microphone;

a source localizing sensor for determining a current location of the sound source;

at least two speakers configured to direct a canceling sound toward a mobile cancellation location that is spatially remote from the sound source and the speakers, a cancellation space localizing sensor for determining a current location of the mobile cancellation space; and a computational module in communication with the source microphone, the source localizing sensor, the speakers, and the cancellation space localizing sensor, the computational module including a memory storing a situational transfer function of individual transfer functions, each individual transfer function corresponding to at least a sound source location and a cancellation space location, the computational module configured to receive a signal from the microphone, to identify at least one current individual transfer function corresponding to the current location of the sound source and the current location of the cancellation location, and to control the speakers to transmit a cancellation sound signal based on the at least one current individual transfer function to the speakers, wherein the situational transfer function includes a situational transfer matrix function, W, $$W=1/(d-c*e)$$

wherein c is a transfer function for sound propagation from the sound source to the source microphone, e is a transfer function for sound propagation from the speaker to the cancellation location, and d is a transfer function for sound propagation from the source microphone to the speaker, and the * operator denotes mathematical convolution.

2. The system of claim 1, further comprising a training sub-system having at least one training microphone that can be placed at the cancellation location.

3. The system of claim 1, further comprising a sound velocity and/or temperature sensor in communication with the computational module, wherein the predetermined adaptive filtering function is responsive to the temperature of the acoustic environment.

4. The system of claim 2, wherein the situational transfer function is determined by receiving a first sound input from the source microphone, receiving a second sound input from the training microphone, and then determining the situational transfer function, wherein the predetermined adaptive filtering function is adaptive to a sound transformation between the source microphone signal and the training microphone signal.

5. The system of claim 1, wherein the situational transfer function comprises a function that identifies a sound transformation between the source microphone and the cancellation location without contemporaneous sound receiving at the cancellation location.

6. The system in claim 1, wherein the source microphone comprises a plurality of source microphones.

7. The system of claim 1, wherein the speaker is a parametric speaker for broadcasting ultrasonic sound, the parametric speaker configured to broadcast a localized cancellation sound at the cancellation location.

8. The system of claim 1, wherein the speaker comprises a plurality of speakers.

9. The system of claim 1 further comprising:

a parametric speaker configured to transmit a canceling sound configured to cancel the detected sound such that the canceling sound is localized with respect to the cancellation location.

10. The system of claim 9, wherein the parametric speaker produces the canceling sound with an interaction between two or more ultrasonic signals.

11. The system of claim 9, wherein the parametric speaker produces the canceling sound by nonlinear interaction of an ultrasonic signal with air.

12. The system of claim 1, wherein the sound source comprises a snoring individual and the speaker spaced apart from the snoring individual.

13. The system of claim 1, wherein the situational transfer function is determined using convolution of the individual transfer functions, and each of the individual transfer functions is configured to characterize propagation of sound with respect to a pair of spaced apart transducers comprising at least one of a speaker, a microphone and/or a velocimeter.

14. The system of claim 1, wherein the at least two speakers are stationary.

15. The system of claim 2, wherein the at least one training microphone is configured to be removed from the cancellation space during transmission of the cancellation signal.

16. The system of claim 1, wherein the situational transfer function comprises a locations-representative situational transfer function representative of a sound source location and a cancellation location.

17. The system of claim 1, wherein the situational transfer function is provided by convolution of individual transfer functions representative of sound propagation between individual speakers, microphones and/or locations.

18. The system of claim 17, wherein the situational transfer function comprises at least one individual transfer function representative of cross talk between the speakers and the microphone.

19. The system of claim 4, wherein the received first sound input comprises undesirable sound from at least one cancellation speaker.

20. The system of claim 1, wherein the individual transfer functions are representative of cross talk and are invariant among the plurality of situational transfer functions.

21. The system of claim 2, wherein the at least one training microphone is deployed, together with one of a head-shaped unit, in a position substantially corresponding to a human ear.

22. The system of claim 1, wherein the individual transfer function includes a cross-talk cancellation feature to reduce a feedback effect of the canceling sound detected by the source microphone.

23. A method of sound cancellation comprising: detecting a sound input at an input location that is spatially remote from a sound source, the sound input including undesirable sound propagating from a mobile sound source remote from the input location; determining a current location of the mobile sound source; determining a current location of a mobile cancellation space; providing a situational transfer function of a plurality of individual situational transfer functions, each individual transfer function corresponding to at least a sound source location and a cancellation space location; identifying a current individual transfer function corresponding to the current location of the sound source and the current location of the cancellation space; and broadcasting a cancellation sound based on the sound input and the current individual transfer function of the situational transfer function for reducing sound proximate the cancellation location, wherein the situational transfer function includes a situational transfer matrix function, W, W=1/(d−e'e) wherein e is a transfer function for sound propagation from the sound source to the source microphone, e is a transfer function for sound propagation from the speaker to the cancellation location, and d is a transfer function for sound propagation from the source microphone to the speaker, and the * operator denotes mathematical convolution.

24. The method of claim 23, further comprising training an algorithm to provide the situational transfer function.

25. The method of claim 24, wherein the training algorithm comprises the steps of:

detecting a first sound at a first location;

detecting a modified second sound at a second location, the modified second sound being a result of sound propagating from the first location to the second location; and determining the situational transfer function, the situational transfer function approximating the second modified sound from the first sound.

26. The method of claim 25, further comprising obtaining a second signal using a training system comprising at least one microphone, the training system being at least one of: head-wearable device and positionable at desired location of cancellation.

27. The method of claim 26, further comprising providing a training device comprising a head surrogate comprising a three dimensional object and at least one microphone.

28. The method of claim 23, further comprising analyzing the sound input for medical screening purposes.

29. The method of claim 23, wherein providing a situational transfer function of individual transfer functions comprises:

detecting first sound at a first location;

detecting a modified second sound at a second location, the modified second sound being a result of sound propagating to the second location;

determining an adaptive filtering function substantially removed of cross talk to provide a cancelling sound for cancelling the second sound;

halting detecting of the modified sound; and determining a cancellation signal proximate the second location from the first sound and the adaptive filtering function.

30. The method of claim 23, wherein providing a situational transfer function of individual transfer functions comprises: detecting a first sound at a first location; detecting a modified second sound at a second location, the modified second sound being a result of sound propagating to the second location; and determining an individual transfer function of the plurality of individual transfer functions based on the first and second location, the individual transfer function approximating the second modified sound from the first sound without requiring additional sound detecting at the second location.

31. The method of claim 23, further comprising:

analyzing a sound input to determine if a change in respiratory sounds occurs sufficient to identify a health condition comprising at least one of: sleep apnea, pulmonary congestion, pulmonary edema, asthma, halted breathing, abnormal breathing, arousal, and disturbed sleep.

32. The method of claim 23, wherein broadcasting a cancellation sound further comprises:

transmitting a canceling signal from a parametric speaker that locally cancels the sound with respect to a cancellation location.

33. The method of claim 32, wherein transmitting a canceling signal further comprises transmitting a plurality of ultrasonic signals wherein the canceling signal is formed from the interaction of the plurality of ultrasonic signals.

34. The method of claim 32, wherein the canceling signal is formed from a nonlinear interaction of an ultrasonic signal with air.

35. The method in claim 32 wherein the canceling signal is formed from an interaction between a plurality of ultrasonic signals that creates a difference signal among the ultrasonic signals at the cancellation location.

36. The method in claim 32 wherein the ultrasonic signal comprises a carrier frequency component and a modulation component and nonlinear interaction between the carrier frequency component and the modulation component in air creates a cancellation sound by demodulation of the ultrasonic signal that is in a generally audible frequency range along the propagation path of the ultrasonic signal.

37. The method of claim 23, wherein the situational transfer function is determined using convolution of the individual transfer functions, and each of the individual transfer functions is configured to characterize propagation of sound with respect to a pair of spaced apart transducer.

38. The method of claim 23, wherein the situational transfer function is provided by a mathematical convolution of the plurality of individual transfer functions.

39. The method of claim 23, wherein the individual transfer functions are representative of at least one sound propagation path comprising: from the sound source to at least one sound source microphone, from the sound source to at least one training microphone, from at least one speaker to at least one training microphone, from at least one speaker to at least one cancellation location, and/or from at least one speaker to at least one sound source microphone being representative of cross talk.

40. The method of claim 25 wherein the training algorithm is provided by determining and mathematically convolving individual transfer functions representing the plurality of sound propagation paths among the source location, the cancellation location, the microphones and the speakers.

41. The method of claim 23, wherein each individual transfer function is representative of the locations of a snorer and bed partner ears and is used selectively to generate a cancellation representative of the locations of the snorer and bed partner ears.

* * * * *